United States Patent [19]
Hansson et al.

[11] Patent Number: 6,080,433
[45] Date of Patent: Jun. 27, 2000

[54] METHOD FOR PRODUCTION OF NUTRITION PHYSIOLOGICAL VALUABLE PRODUCTS AND A PLANT FOR ACCOMPLISHING THE METHOD

[75] Inventors: Bengt Hansson, Löddeköpinge; Rolf Bergkvist, Åkarp, both of Sweden

[73] Assignee: Biowheat AB, Loddekopinge, Sweden

[21] Appl. No.: 09/051,270

[22] PCT Filed: Oct. 7, 1996

[86] PCT No.: PCT/SE96/01266

§ 371 Date: Apr. 6, 1998

§ 102(e) Date: Apr. 6, 1998

[87] PCT Pub. No.: WO97/12525

PCT Pub. Date: Apr. 10, 1997

[30] Foreign Application Priority Data

Oct. 6, 1995 [SE] Sweden .................................. 9503473

[51] Int. Cl.[7] .............................. C12P 19/14; A23L 1/105
[52] U.S. Cl. ................................ 426/28; 426/18; 426/64; 426/618; 435/72

[58] Field of Search ................................... 426/28, 49, 52, 426/61, 615, 618, 622, 64; 435/95–99, 100, 72

[56] References Cited

U.S. PATENT DOCUMENTS 4,710,386 12/1987 Fulger et al. .............................. 426/28
5,082,673 1/1992 Inglett ....................................... 426/21

FOREIGN PATENT DOCUMENTS 0078782 11/1983 European Pat. Off. .

*Primary Examiner*—Keith D. Hendricks
*Attorney, Agent, or Firm*—Klarquist Sparkman Campbell Leigh & Whinston, LLP

[57] ABSTRACT

A process for the preparation of nutritionally valuable products from cereals by means of an enzymatic degradation of the starch present in the cereals is provided. Gelatinization and degradation of the starch to soluble dextrines and their continued degradation to more simple oligosaccharides is carried out in a single step. Additionally, a plant for carrying out the process is provided.

13 Claims, 6 Drawing Sheets

METHOD FOR PRODUCTION OF NUTRITION PHYSIOLOGICAL VALUABLE PRODUCTS AND A PLANT FOR ACCOMPLISHING THE METHOD

This application is a 371 of PCT/SE96/01266, filed Oct. 7, 1996.

TECHNICAL FIELD

The present invention relates to a process for preparing nutritionally valuable products from cereals by means of an enzymatic degradation of the starch present in the cereals to soluble dextrines and in turn their continued degradation to more simple oligosaccharides in one step, as well as a plant for carrying out the process.

The object of the present invention is to provide a possibility of obtaining nutritionally valuable products from cereals in a simple and rational way, which products are to be used in human and animal applications.

A further object is to obtain a strongly simplified and time-saving process which enables production of products having different amounts of glucose. Hereby different cereals or fractions of cereals can be used as starting materials, such as wheat, oat, barley, rye, maize, sorghum as well as other starch products.

In certain applications the end product can be used directly and does not require drying or further fractionation or drying. In those cases where a dried product is desired, the end product can be dried by spray drying, or varieties thereof, or by a roller dryer. In certain cases the fiber component of the product is separated and dried on its own and used as a high value and pleasant tasting nutritional fibrous product.

A further other object of the invention is to provide a production plant for the process of the invention, particularly for a continuos production.

BACKGROUND OF THE INVENTION

It is known, for instance, from SE-A-7808870-5 to hydrolyze whole cereal grains using protein and starch degradable enzymes. The method disclosed leads to a more complex production process taking 15–30 hrs to carry out to obtain a high content of glucose. These long processing times also leads to the fact that very large plants are needed to be able to produce a larger amount of product. Such a process is further difficult to carry out as a continuos process due to the long retention times. These previously known processes primarily involve the degradation of protein using a proteolytic enzyme at 60° C. (for 2 hours), followed by addition of an alpha-amylase at 75° C., and degradation of starch to form polysaccharides (for 6 hours), followed by the addition of an amyloglucosidase for further degradation of polysaccharides.

It has now surpringly been shown possible to be able to rationalize the production of glucos containing products from cereals by means of the present process and thereby obtaining considerably shortenend production times, which means that the process can be developed into a continous process.

The present invention further comprises a plant suitable for carrying out the present process.

DESCRIPTION OF THE PRESENT INVENTION

The present invention is characterized in that the gelatinization and degradation of the starch to soluble dextrines and their continued degradation to more simple oligosaccharides is carried out in one step.

This is achieved by means of the invention by already in a first phase adding alpha-amylase and amyloglucosidas at the same time as the conditions concerning pH and temperature are so adjusted that the different types of enzymes have a satisfactory activity.

Hereby a rapid degradation of the starch is obtained avoiding the normally existing, very considerable increase of the viscosity obtained in the beginning of a gelatinization. More simple and less cost demanding stirrer systems can thus be used. Simultaneously a very rapid enzymatic degradation of the starch into more simple carbohydrates is obtained and already after a few hours a maximum of the glucose content can be obtained.

The process further means that the product may contain a mixture of glucose and maltose by choosing a suitable amount of amyloglucosidase and predetermined incubation time.

As mentioned above crushed whole grains of wheat, oat, barley, rye, maize and sorghum can be used as starting materials. The particle size is hereby not essential to the process as such but is rather determined by the final drying method used alternatively, the fractionation of the end product and application use. Also flours of these cereals can be used as well as other raw materials rich in starch.

The process is carried out in a suitable reaction vessel provided with a stirrer and having means for to maintaining a desired temperature. However, in the present application there is further disclosed a preferred plant for a continous production which plant comprises a blending and heating unit, heat exchangers, reaction vessels, and end reaction vessel.

Generally, the raw material while being stirred is provided with water preheated to 40 to 75° C., preferably 40 to 60° C. and provided with alpha-amylase as well as an amyloglucosidase, whereby the temperature of the total mixture is at most 55° C.

Suitable alpha-amylases are Termamyl (reg. trademark) 120L (Novo), BAN 240L (Novo) or the corresponding. A suitable amyloglucosidase is AMG 200L (Novo) or the corresponding. These enzymes as mentioned are present in liquid form and are thus easy to add in correct dose. When Termamyl is used less Ca-ions are needed in the solution.

When about 30 to 50% of the starch containing raw material has been added an adjustment of the pH is made to 4.5 to 5.5, suitably pH 4.9 using hydrochloric acid or citric acid or another suitable acid. Then the temperature is raised to a range of 60 to 75° C. until the reaction product has obtained the composition desired with regard to its glucose content. Simultaneously herewith the gelatinization which is important to the process, is obtained, which however, due to a certain degradation of the starch already has happened does not lead to such an increase of the viscosity that should have been obtained if the starch had not already been partly degraded. Then the enzymes are inactivated by heating of the reaction product to 90 to 95° C., alternatively 125 to 130° C. for 30 to 60 sec. depending on the thermostability of the amyloglucosidase used. Simultaneously there is a sterilization of the product.

The end product can now be used directly for certain applications and in other applications first after having been dried, concentration to a suitable water content. Storage of the product can be done in suitable designed vessels depending of the end use. In particular one should consider the maintaining of the sterility. Aseptic packaging is thus possible and suitable.

As mentioned above the end product can also be spray dried or be roller dried. If a fiber fraction is separated off this is preferably dried in a drier using heated air.

The invention will be described more in detail in the following with reference to some non-limiting examples.

EXAMPLE 1
Productiion of a Glucose Enriched Product Starting from Wheat Flour

Figure 1:
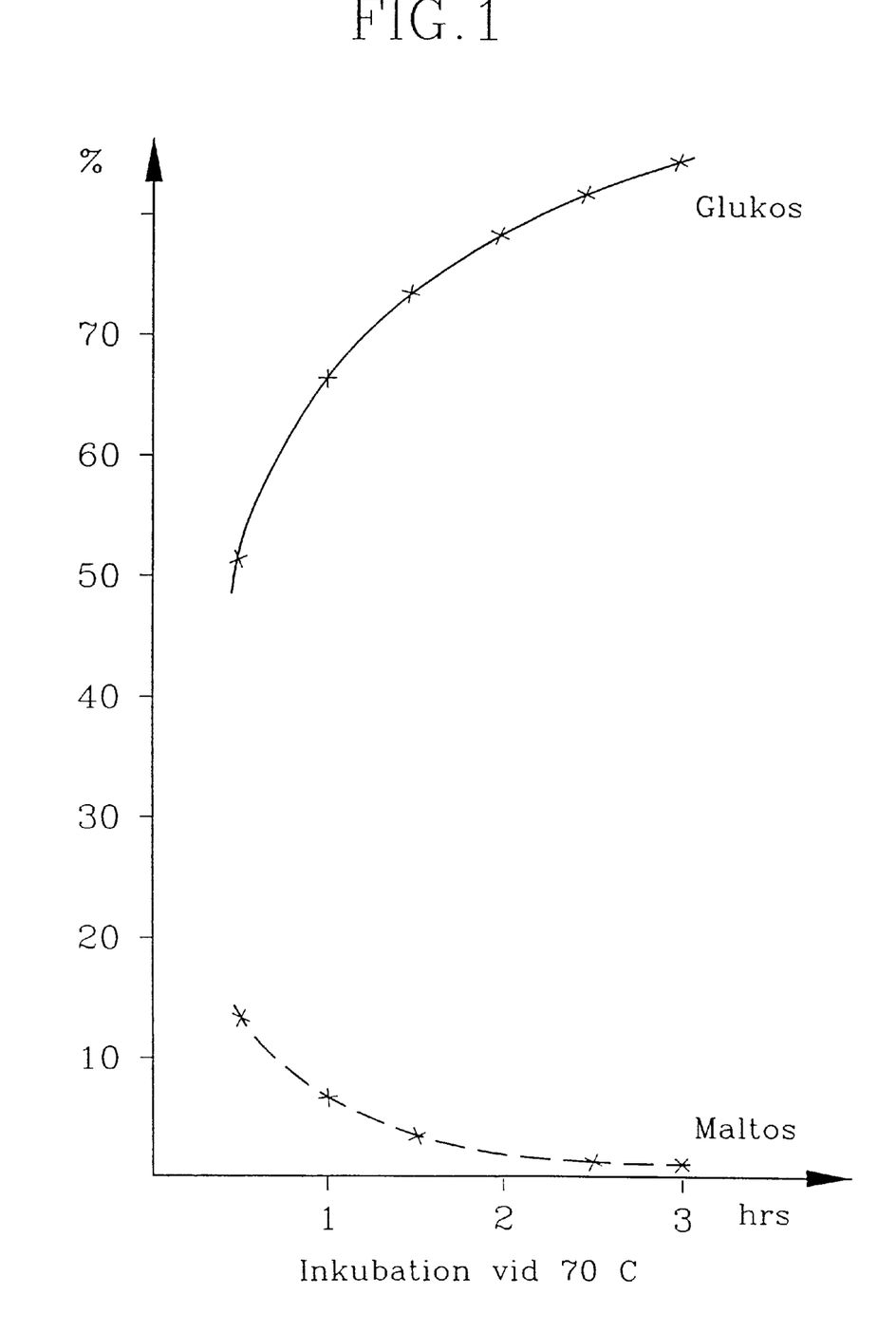
FIG. 1 is a graph illustrating the percentage increase in carbohydrate solubility against time for glucose and maltose at 70° C.

As raw material a conventional wheat flour was used, whereby 500 g of wheat flour are added while being stirred to 1000 ml of water heated to about 55° C., which water contains 1.0 ml of Termamyl 120L and 2.0 ml of AMG 200L. When about 50% of the wheat flour had been added pH is adjusted to 4.9 by adding a diluted hydrochloric acid, whereupon, when all the wheat flour had been added, further diluted hydrochloric acid is added to said pH. The temperature of the mixture is then raised to 70 to 75° C., simultaneously as the content of simple carbohydrtaes formed is succesively determined using HPLC. The increase of simple carbohydrates in the soluble part is evident from FIG. 1. After 3 hrs at 70° C. the incubation is brought to a stop by inactivating the enzymes by heating using micro waves to 95° C., whereby the product is simulaneously being sterilized.

After drying a product is obtained having a sweet taste comprising 68% of glucose EXAMPLE 2
Production of a Glucose Enriched Product Starting from Whole Wheat Whole wheat grains are milled to a particle size of 0.05 to 1.5 mm. 700 g of the wheat are added while being stirred to 1000 ml of water having a temperature of 55° C. and comprising 1.0 ml of Termamyl 120L and 2.0 ml of AMG 200L. When about 50% of the wheat has been added pH is adjusted to 4.9 by adding diluted hydrochloric acid and then when all the wheat has been added a further addition of hydrochloric acid. The amount of hydrochloric acid is depending on the buffering capacity of the raw material. The temperature of the mixture was then raised to 70 to 75° C. during a continued stirring, whereby the incubation continues. The amount of simple carbohydrates is determined using HPLC. After 3 hrs at 70° C. the inubation is stopped and the product is sterilized and the enzymes are deactivated by heating to 95° C.

After drying a sweet product is obtained having a glucose content of 55%.

EXAMPLE 3
Production of a Glucose Enriched Product Starting from Oat

Whole oat grains having been freed from its sticky casing are milled to a fine flour having the approximate particle size as in Example 2. 700 g of the flour are added to 1000 ml of water heated to 55° C. and containing 1.5 ml of Termamyl 120L and 2.5 ml of AMG 200L. When about 50% of the flour has been added pH is adjusted by adding hydrochloric acid and pH is then finally adjusted to 4.9 by adding hydrochloric acid when all the oat has been added. The temperature of the mixture was then raised to 70 to 75° C. during a continued stirring, whereby the incubation continues. The amount of simple carbohydrates is determined using HPLC. After 3 hrs at 70° C. the inubation is stopped, and the product is sterilized, and the enzymes are deactivated by heating to 95° C. The dry content of the soluble part then 71% consisted of glucose.

After drying a sweet product having a mild taste of oat is obtained and having a glucose content of 59%.

In the examples above 33 to 41% amount of dry content has been used for the mixture of the raw material in the water. This amount can, however, be increased to 50% without any greater problem, whereby the optional need for drying is reduced, as well as the product can more easily be used in the direct production of food stuffs, such as bakery products.

In the examples above alpha-amylase has been used together with amyloglucosidase. Alpha-amylase can be used in combination with beta-amylase if so desired.

The end product can be used as a general food stuff additive in stead of sugar, such as in bakery products, ketchup, ice-cream and other products.

The product prepared provides an increased degree of creaminess to the product in which it is used such as in drinks and others.

Figure 2:
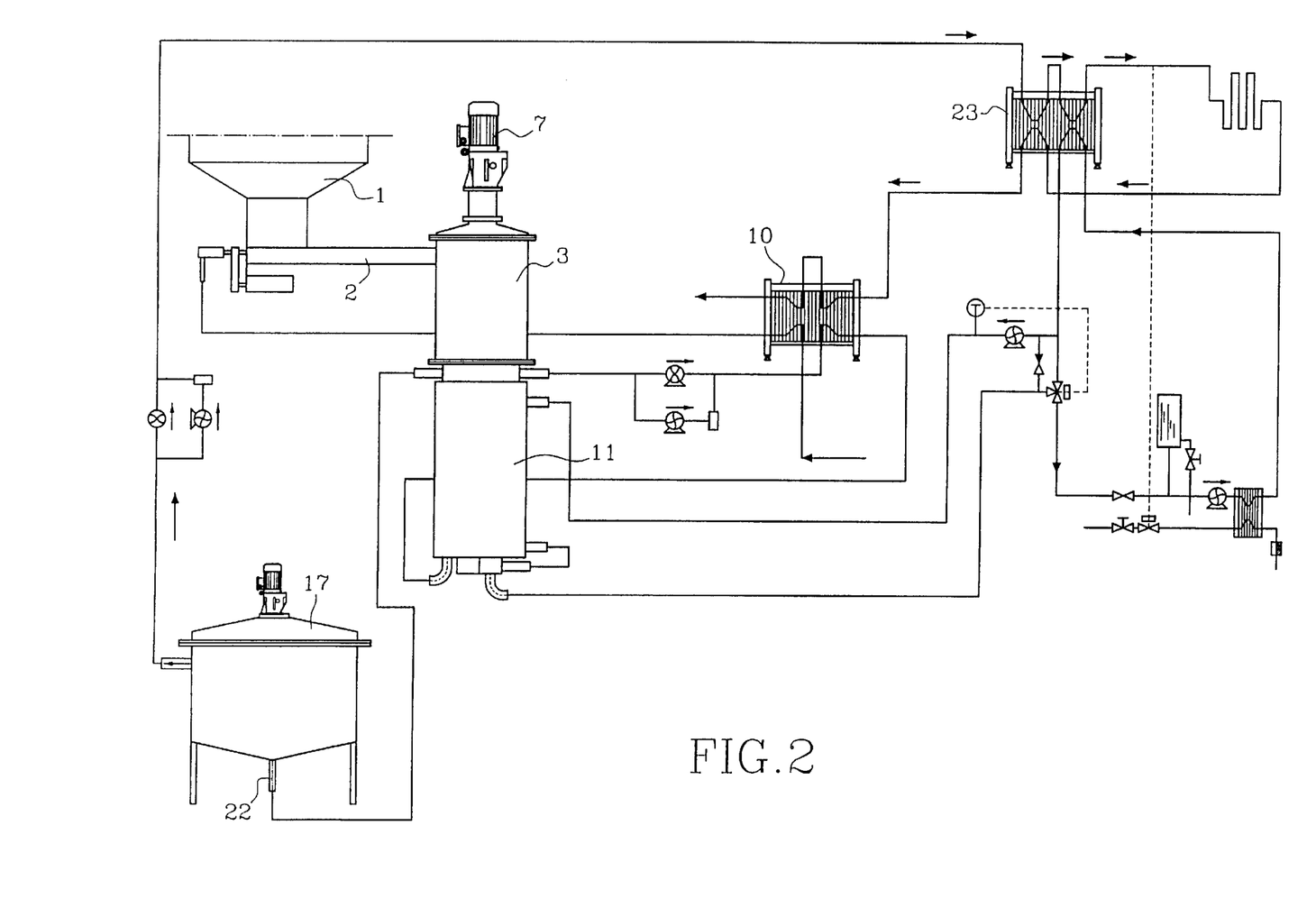
FIG. 2 is a schematic diagram of an embodiment of a plant as described herein.
Figure 3:
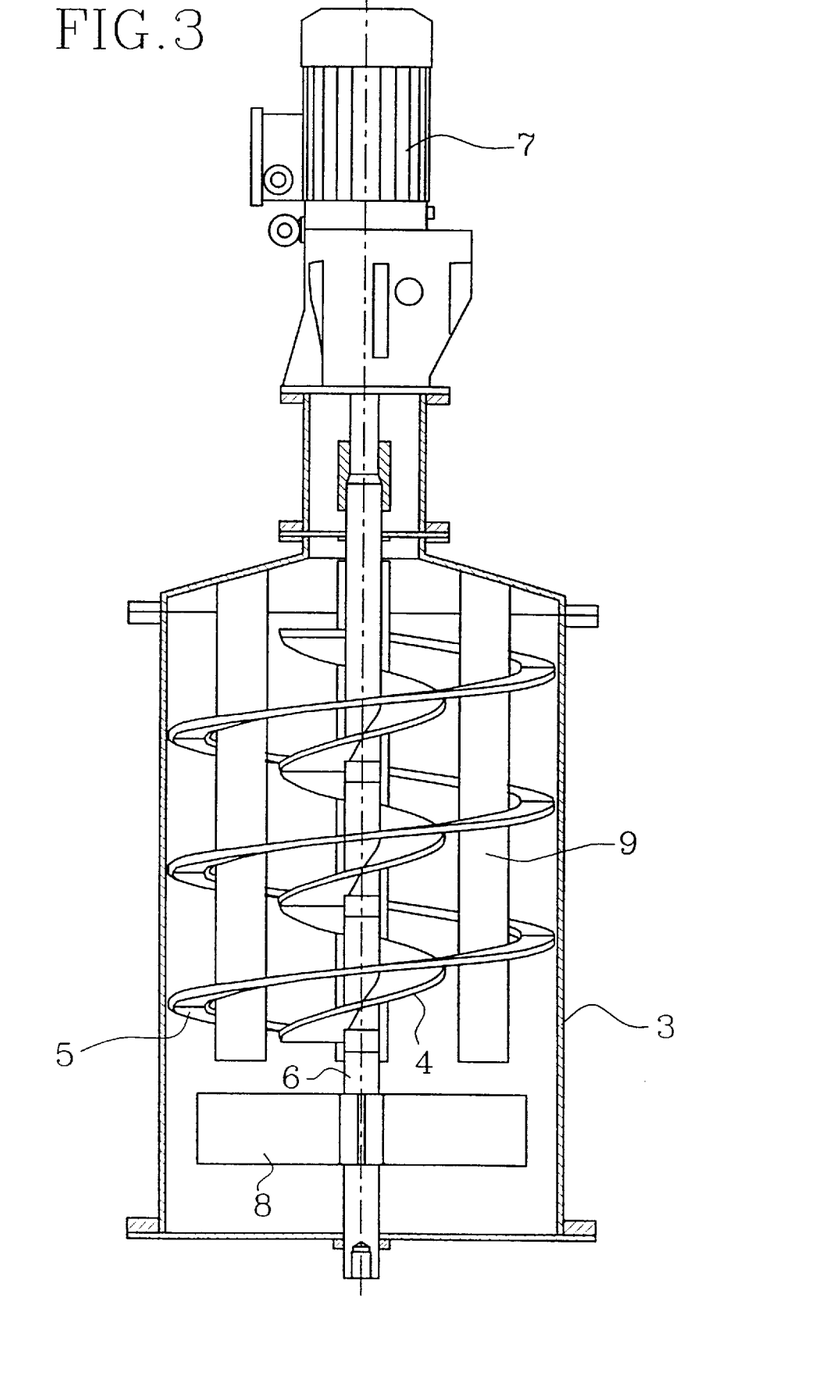
FIG. 3 is a cross-sectional diagram of a blending reactor.
Figure 4:
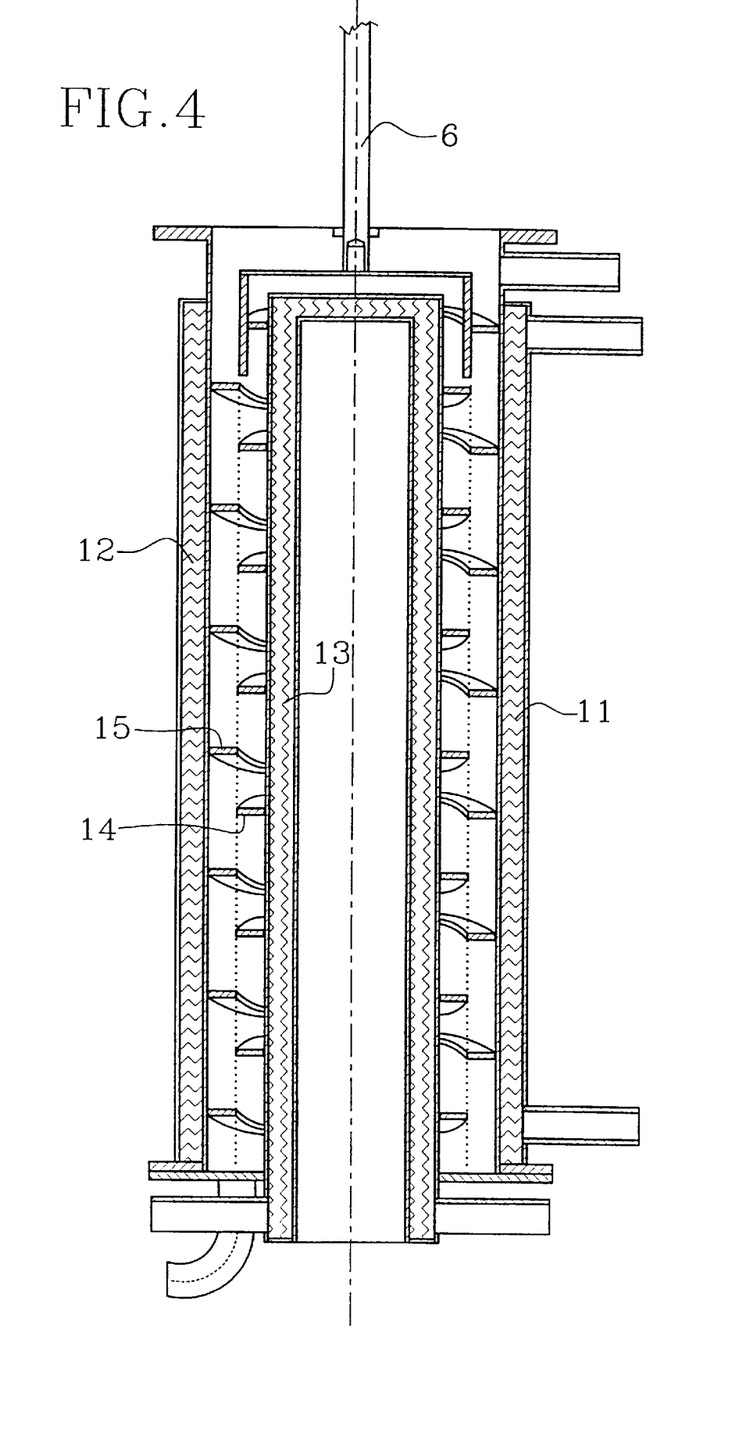
FIG. 4 is a cross-sectional diagram of a reaction reactor.
Figure 5:
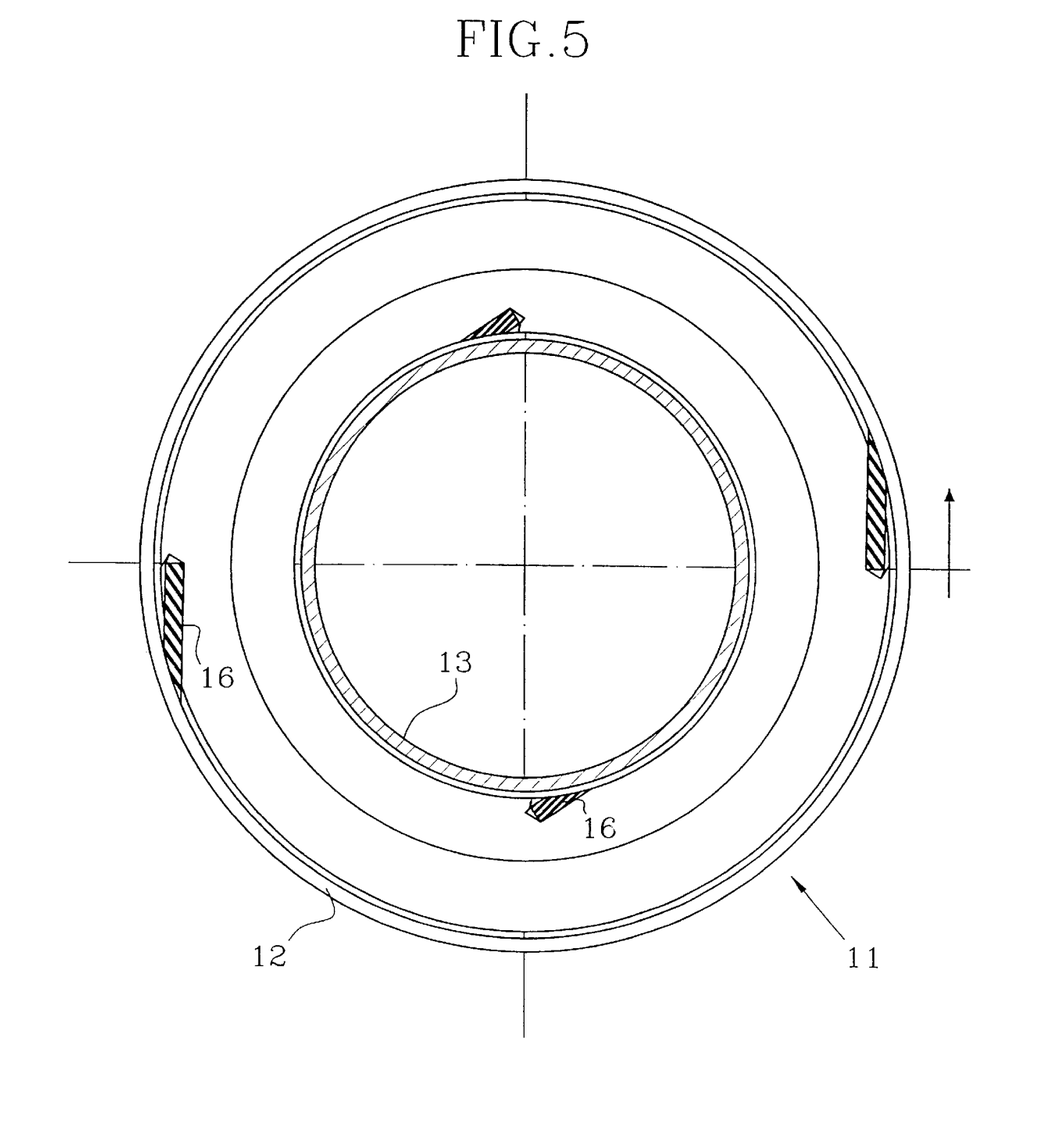
FIG. 5 is a cross-sectional diagram of the reaction reactor shown in FIG. 4.
Figure 6:
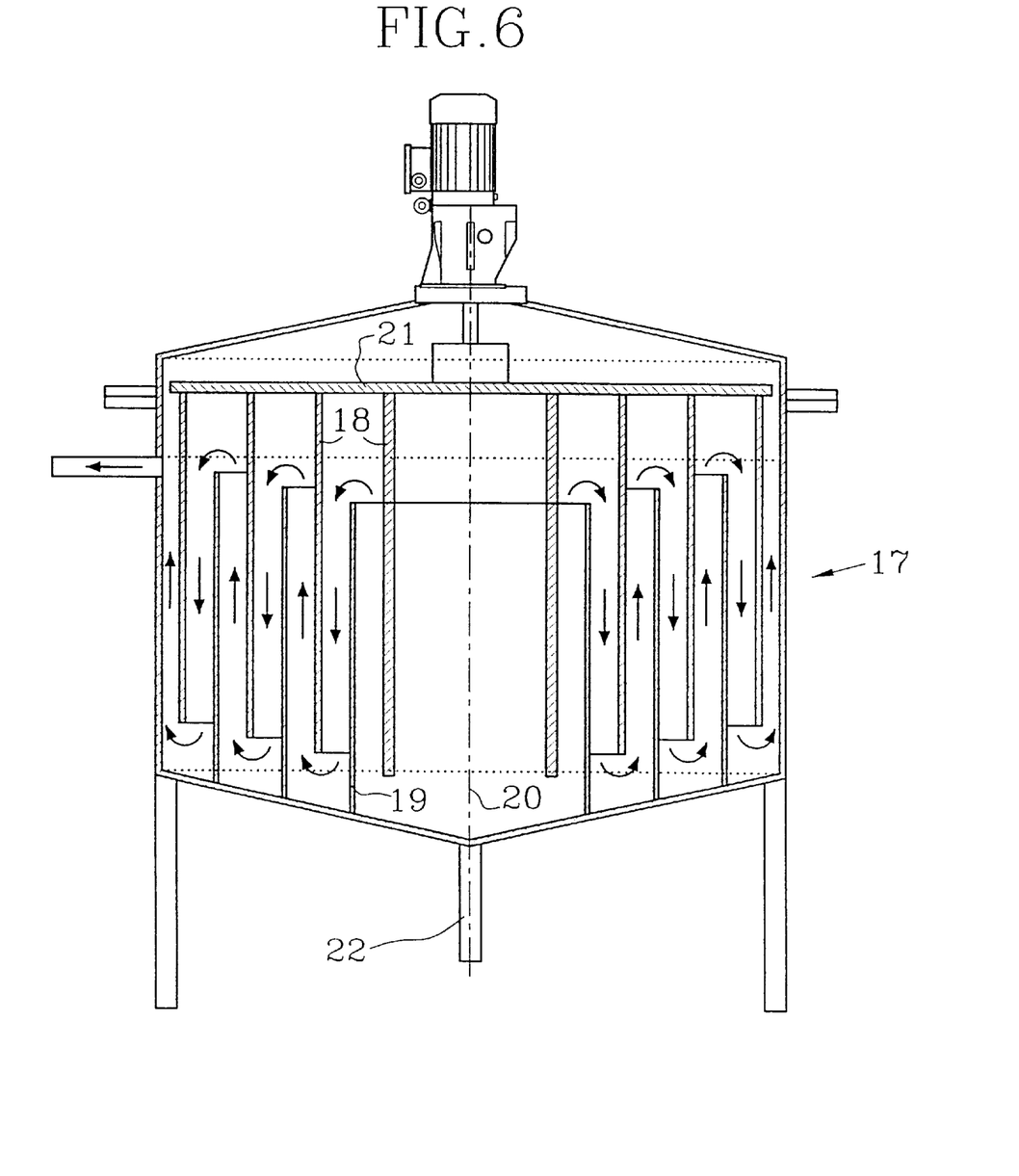
FIG. 6 is a cross-sectional diagram of an end incubation reactor.

As mentioned above the present invention relates to a plant for carrying out the present process as well, during continous conditions. This part of the invention will be described more in detail with reference to the attached drawing, wherein FIG. 2 shows a plant in general;

FIG. 3 shows a blending reactor of the plant in cross-section;

FIG. 4 shows a reaction reactor of the plant in cross-section;

FIG. 5 shows the reaction reactor of FIG. 4 in cross-section in a plane perpendicular to the rotational axis; and FIG. 6 shows an end incubation reactor of the plant in cross-section.

A preferred plant for carrying out the process according to the invention is shown in general in FIG. 2. The flour of a suitable origin is fed into a storage container 1, from which container 1 the flour is then fed to a transporting screw 2 up to a prereactor 3. Before the flour is being introduced into the prereactor 3 water is added in a suitable amount and having a suitable temperature in relation to the flour in such a way that the water content is about 50% and the temperatre is about 50° C. The enzymes needed for the hydrolysis of the starch present are dissolved or suspended in the water. The prereactor comprises, as shown in FIG. 3, two helical screws 4 and 5, whereby the inner one 4 is mounted directly to the throughgoing shaft 6 which is driven by a motor 7 with a speed of about 100 rpm, and whereby the outer helical screw is mounted to and driven via a paddle stirrer 8 in the lower part of the reactor. Between the two helical screws 4 and 5 athere are one or more stationary stirring means 9 which lead to the fact that the starch-water-mixture, which primarily has a very high viscosity not only accompany the screw movement but is mixed as well. As the helical screws have opposite rise but are driven at the same direction will, in the example, the inner helical screw 4 drive the material downwards, while the outer helical screw lifts the material. The contracting movements leads to a very high degree of homogenization of the material. Thus the downwardly directed movement in the centre of the reactor, according to the embodiment, that the material is compressed in order to then become loosened during the raising movement in the periphery of the reactor. After a retention time of "some" minutes the flour-water-mixture is fed out in the form of a slurry from the prereactor whereby the temperature is 48 to 50° C. The slurry is then fed using a pump to a heat exchanger 10 where the temperature is raised to about 60° C. and then to 70° C., whereupon the slurry is fed to second reactor 11 (FIG. 4). At the heating to 70° C. the gelatinazation being important to the process takes place, whereby a marked increase in viscosity is obtained. The slurry is introduced in the lower part of this reactor and is transported upwards through the reactor by means of the pressure from the pump. The second reactor 11 comprises a jacketed outer surface 12 and a central cylindrical body 13, which is jacketed as well. The reactor further comprises two helical screws 14 and 15, which are driven by a common motor. In the embodiment according to the present FIG. 2, FIG. 3 and FIG. 4 they are driven by the motor 7. In this reactor 11, as well, the helical screws 14 and 15 are contrary rotating, i.e. the one 15, the outer one, presses the material downwardly, while the other, 14, the inner one, lifts the material. The helical screws are arranged in such a way that there is a smaller gap between the jacketed surface 12 and the jacketed surface 13. As these surfaces are hot the material may adhere to these surfaces and in order eliminate this the respective helical screw is provided with vertical scraping elements 16 which are placed in recesses in their respective helical screw 14 or 15 (FIG. 6). The scraping elements 16 are suitable made of an inert material visavi the slurry and can be simply exchanged from either side of the reactor, suitably from above. After having passed the reactor 11 during heating by adding heat to the two jacketed surfaces 12 and 13 the slurry is removed from the upper part of the reactor 11. The slurry is hereby transferred to the incubation reactor (FIG. 5) for the final hydrolysis, whereby the retention time in this incubation reactor 17 is about 2 hrs. The incubation reactor 17 comprises a number of concentricly arranged cylindrical walls 18 and 19, whereby every second one, 19, is arranged from the bottom 20 and every second, 18, is arranged from the top 21 of the reactor. The inner cylinder 18 may also consist of staffs. The cylinders 18 and 19 respectively, do not pass through the entire height of the reactor but ends somewhat above the bottom 20 of the reactor, and somewhat below the top 21 of the reactor. The cylinders 18 arranged to the top 21 of the reactor are rotably arranged via the motor arranged to the upper part of the reactor. The rotation may hereby be either single directed or alternating double directed. The material, the slurry, is introduced centrally in the bottom of the reactor through an inlet 22. As the cylinders do not cover the entire the whole height of the reactors, gaps are formed over, or below the respective cylinder wall above and below, respectively, the slurry can pass such has been marked with arrows in FIG. 3. Subsequent to the incubation 17 the slurry is fed by means of a pump to a heat exchanger 23 where the temperature is raised to 110 to 120° C. in order to deactivate the enzymes. The slurry is then fed again through the same heat exchanger 23 in order to make use of its heat for heating of later incoming slurry and cooling before it is fed further to the first heat exchanger 10, where the temperature is once again about 50° C. The slurry is being heat exchanged in the final step suitably against cold water which is used as ingoing water in the preparation of a new slurry in the blending step, whereby this water obtains the right temperature for the blending and thereby the hydrolysis.

What is claimed is:

1. A process for the preparation of nutritionally valuable products from starch-containing cereals by means of an enzymatic degradation of the starch present in the cereals, comprising:

(a) gelatinization of the starch;

(b) degradation of the starch to soluble dextrines; and (c) continued degradation of the soluble dextrines to more simple oligosaccharides, wherein (a), (b), and (c) are carried out in one step, wherein enzymes used for the degradation are added to cereal raw material via ingoing liquid used for slurrying and heating the cereal raw material, and wherein the temperature of the ingoing liquid is 40° C. to 75° C., the amount of water used in the ingoing liquid is 40% to 67% by volume of the total ingoing liquid, and wherein the remainder of the ingoing liquid by volume comprises cereals and enzymes.

2. A process according to claim 1, wherein the temperature of a final liquid, comprising water, cereals and enzymes is 55° C.

3. A process according to claim 1, wherein the amount of water in the ingoing liquid is 50% by volume, and wherein the remainder by volume comprises cereals and enzymes.

4. A process according to claim 1, wherein the temperature of the ingoing liquid is 40° C. to 75° C., and wherein the temperature of the final liquid, said final liquid comprising water, cereals and enzymes, is at most 55° C.

5. A process according to claim 1, wherein the temperature of the reaction product after blending of the ingoing ingoing liquid comprising enzymes is raised to a temperature of between 60° C. and 75° C. while gelatinization occurs.

6. A one-step process for the production of a glucose-enriched product from cereal starch, comprising:

(a) gelatinization of a cereal starch;

(b) enzymatic degradation of the cereal starch to soluble dextrines; and (c) enzymatic degradation of the soluble dextrines to one or more simple sugars, wherein at least one of the simple sugars is glucose, and wherein (a), (b), and (c) are carried out in a single step, in a single reaction vessel.

7. The process of claim 6, wherein the cereal starch, enzymes, and preheated water are mixed together in a single reaction vessel to form a mixture, and wherein the initial temperature of the mixture is form 40° C. to 55° C.

8. The process of claim 7, including at least one enzyme selected from the group consisting essentially of: an alpha-amylase, a beta-amylase, an amyloglucosidase, and mixtures thereof.

9. The process of claim 8, wherein the enzyme comprises an alpha-amylase.

10. The process of claim 8, wherein the glucose-enriched product, has a dry weight glucose content of from 55% to 71%.

11. The process of claim 10, wherein, after 30% to 50% of the cereal starch has been added to the reaction vessel, the pH of the mixture is adjusted to be from 4.5 to 5.5, and wherein the temperature of the mixture is raised to from 60° C. to 75° C.

12. The process of claim 10, wherein the process is carried out in a blending reactor, a reaction reactor, or an incubation reactor.

13. The process of claim 11, wherein the process is carried out in a blending reactor, a reaction reactor, or an incubation reactor.

* * * * *

UNITED STATES PATENT AND TRADEMARK OFFICE
CERTIFICATE OF CORRECTION

PATENT NO. : 6,080,433
DATED : June 27, 2000
INVENTOR(S) : Bengt Hansson and Rolf Bergkvist It is certified that error appears in the above-identified patent and that said Letters Patent is hereby corrected as shown below:

Title page,
After PCT Filed:, delete "Oct. 7, 1996" and insert -- Apr. 6, 1998 --.

Column 6,
Line 29, delete the first "ingoing".
Line 46, delete "form" and insert -- from --.

Signed and Sealed this

Twenty-fifth Day of December, 2001

Attest:

Attesting Officer

JAMES E. ROGAN
Director of the United States Patent and Trademark Office